US009532710B2

(12) United States Patent
Biernat et al.

(10) Patent No.: US 9,532,710 B2
(45) Date of Patent: Jan. 3, 2017

(54) FLEXIBLE, MULTIMODAL RETINA IMAGE RECORDING SYSTEM AND MEASUREMENT SYSTEM

(71) Applicant: CARL ZEISS MEDITEC AG, Jena (DE)

(72) Inventors: Detlef Biernat, Jena (DE); Markus Strehle, Jena (DE); Axel Waldheim, Kahla (DE); Dietrich Martin, Jena (DE); Martin Hacker, Jena (DE); Eberhard Hagen, Jena (DE); Martin Kühner, Bad Klosterlausnitz (DE); André Meyer, Jena (DE)

(73) Assignee: Carl Zeiss Meditec AG, Jena (DE)

( * ) Notice: Subject to any disclaimer, the term of this patent is extended or adjusted under 35 U.S.C. 154(b) by 0 days.

(21) Appl. No.: 14/441,108

(22) PCT Filed: Nov. 7, 2013

(86) PCT No.: PCT/EP2013/073261
§ 371 (c)(1),
(2) Date: May 6, 2015

(87) PCT Pub. No.: WO2014/072400
PCT Pub. Date: May 15, 2014

(65) Prior Publication Data
US 2015/0294458 A1 Oct. 15, 2015

Related U.S. Application Data

(60) Provisional application No. 61/723,890, filed on Nov. 8, 2012.

(30) Foreign Application Priority Data

Nov. 8, 2012 (DE) .......................... 10 2012 022 058

(51) Int. Cl.
*A61B 3/10* (2006.01)
*A61B 3/14* (2006.01)
(Continued)

(52) U.S. Cl.
CPC ............ *A61B 3/102* (2013.01); *A61B 3/0058* (2013.01); *A61B 3/0091* (2013.01); *A61B 3/12* (2013.01);
(Continued)

(58) Field of Classification Search
CPC ............ A61B 3/102; A61B 3/12; A61B 3/14; A61B 3/0025; A61B 3/0058; A61B 3/1025; A61B 3/0008; A61B 3/1225; A61B 3/152; A61B 5/0066; A61B 3/10; A61B 3/0075; A61B 3/0091; A61B 3/113; A61B 18/201; A61B 19/54; A61B 2019/5483; A61B 2090/3983; A61B 3/1241; A61B 3/145; A61B 3/154; A61B 5/0059; A61B 5/0073; A61B 5/7445; A61B 8/10; A61B 1/0019; A61B 3/0033; A61B 3/0041; A61B 5/0261; A61B 5/411; A61B 5/6821; A61B 5/7278; A61B 5/742; A61F 2009/00851; G01B 9/02091; G01B 9/0203; G01B 2290/65; G01B 9/02007; G06T 2207/30041; G06T 7/0012; G06T 2207/10101; G02B 27/141; G03B 13/32

See application file for complete search history.

(56) References Cited

U.S. PATENT DOCUMENTS 5,537,162 A 7/1996 Hellmuth et al.
5,847,806 A 12/1998 Mihashi
(Continued)

FOREIGN PATENT DOCUMENTS

EP 1 952 755 A1 8/2008
EP 2 179 688 A1 4/2010

OTHER PUBLICATIONS

PCT International Search Report and Written Opinion for PCT/EP2013/073261, mailed Apr. 11, 2014, 15 pgs.

*Primary Examiner* — Manav Seth
(74) *Attorney, Agent, or Firm* — Patterson Thuente Pedersen, P.A.

(57) ABSTRACT

A fundus camera with an OCT measurement module, in which, after the focusing objective, a mirror switches the light to be detected either to the OCT measurement module or an image detector. This design also renders it possible to carry out a method for improved focusing in order to improve the recording quality of the individual modalities. Furthermore, the multimodal measuring instrument distinguishes itself by an operating concept according to the
(Continued)

invention. Such combination instruments are advantageous in that, as a result of the reduction from two instruments to one, less space is required than in the case of two separate instruments. Furthermore, reseating of the patient is avoided if recordings or measurements of different modalities should be made for one and the same patient, as a result of which the procedures in the medical practices and clinics can be influenced positively.

12 Claims, 3 Drawing Sheets

(51) Int. Cl.
*A61B 3/12* (2006.01)
*A61B 5/00* (2006.01)
*A61B 3/00* (2006.01)
*G06T 7/00* (2006.01)
*G06T 11/00* (2006.01)

(52) U.S. Cl.
CPC .............. *A61B 3/14* (2013.01); *A61B 5/0066* (2013.01); *G06T 7/0012* (2013.01); *G06T 11/003* (2013.01); *G06T 2207/10101* (2013.01); *G06T 2207/30041* (2013.01)

(56) References Cited

U.S. PATENT DOCUMENTS

| | | | |
|---|---|---|---|
| 7,777,893 B2* | 8/2010 | Kikawa | G01N 21/4795 356/479 |
| 7,784,942 B2* | 8/2010 | Maeda | A61B 3/1241 351/205 |
| 7,824,035 B2* | 11/2010 | Yamada | A61B 3/102 351/206 |
| 2007/0159595 A1 | 7/2007 | Fukuma et al. | |
| 2007/0222946 A1 | 9/2007 | Fukuma et al. | |
| 2007/0291277 A1 | 12/2007 | Everett et al. | |
| 2011/0043757 A1* | 2/2011 | Everett | A61B 3/102 351/208 |
| 2011/0181702 A1* | 7/2011 | Hauger | A61B 3/102 348/46 |
| 2012/0121158 A1 | 5/2012 | Sekine et al. | |

* cited by examiner

FLEXIBLE, MULTIMODAL RETINA IMAGE RECORDING SYSTEM AND MEASUREMENT SYSTEM

RELATED APPLICATIONS

This application is a National Phase entry of PCT Application No. PCT/EP2013/073291 filed Nov. 7, 2013, which application claims the benefit of priority to German Application No. 10 2012 022 058.8, filed Nov. 8, 2012, and claims the benefit of priority to U.S. Application No. 61/723,890, filed Nov. 8, 2012, the entire disclosures of which are incorporated herein by reference.

BACKGROUND

In recent years, optical coherence tomography (OCT) has established itself as routine modality for diagnosing retinal disorders. Because of its 2D slice data records or 3D data records of the retina, it complements the previous conventional fundus recordings such as color recordings and fluorescence angiography recordings and also the more recent autofluorescence recording measurements and macula pigment measurements by the fundus cameras. In so doing, fundus camera recordings and OCT measurements were previously, for reasons of instrument complexity, made in different instruments. The procedures were designed accordingly, particularly in the large clinics as well. It is only in the last few years that combination instruments have also been commercially available, which are able to make both fundus camera recordings and OCT measurements.

Such combination instruments are advantageous in that, as a result of the reduction from two instruments to one, less space is required than in the case of two separate instruments. Furthermore, reseating of the patient is avoided if recordings or measurements of different modalities should be made for one and the same patient, which has a positive influence on the procedures in the medical practices and clinics. However, the existing combination instruments have a number of deficiencies.

In the existing combination instruments, fundus camera recordings and OCT measurements occur simultaneously or shortly one after the other, as described in US 2007/159595, and the signals of the modalities are separated by a dichroic mirror, as likewise described in US 2007/159595 or as already described in U.S. Pat. No. 5,537,162. If fundus images and OCT signals are recorded simultaneously, it is possible to register both modalities laterally to one another without movement artifacts, but the signal strength of both modalities is reduced compared to an individual measurement since, for safety reasons, the maximum illumination intensity permissible for the eye must be divided between both/several simultaneously recorded modalities. To the extent that the wavelengths to be separated are far apart, dichroic mirrors can be used with great efficiency. However, the increasing number of modalities and optical assistance functions, such as fixation, positioning and focusing aids, lead to the wavelength regions to be separated lying ever closer together, and so the separation efficiency of the dichroic mirrors reduces and hence the signal intensity of the individual modalities is also reduced. In the existing combination instruments, the assistance functions of a conventional fundus camera are furthermore inherited and employed in the same manner as is conventional for conventional fundus cameras. Aligning the camera on the eye in order to minimize reflections at the cornea takes place using positioning markers and the focusing on the retina takes place using focusing markers; both in the IR (infrared) live image from the fundus camera. The positioning/focusing settings for the other modalities are then coupled to the recording settings of the focused IR live image in the same fixed manner for all patients. In particular, the focus position of the OCT and of the fundus recording is fixedly coupled to the focus position of the focused IR live image. This rigid coupling leads to the focus setting not being optimal for every one of the modalities, such as color recordings or fluorescence angiography recordings, and/or not being optimal for each examination object in the retina, such as the nerve fiber layer or the pigment epithelium, and/or not being undertaken in an optimal manner for each patient. This non-optimal focusing then leads to fine lateral structures of the examination objects possibly no longer being sensed correctly.

Furthermore, the procedure of the measurements of the individual modalities in existing combination instruments is strongly oriented toward predefined application problems. By way of example, this is described in US 2012/121158. In accordance with US 2012/121158, different measurement procedures consisting of measurements from different modalities and the associated recording parameters thereof are predefined for different problems such as macula disorders or glaucoma disorders. Then, in order to measure a patient, one problem or measurement procedure is selected and the measurements defined in the measurement procedure are carried out. An advantage of this is that the measurement procedure ensures that all recordings required to diagnose a clinical picture are in fact also made.

However, this also has the following disadvantages: by way of example, if glaucoma is suspected and a measurement procedure which comprises the optic nerve papilla in an OCT measurement and in a fundus recording is started for the patient, it is subsequently possible to start a measurement procedure for examining a macula disorder using an OCT measurement and a fundus recording of the macula, but this is only expedient in the state of the eye dilated by drops since the first fundus recording would otherwise lead to pupil narrowing, making the measurement of the second measurement procedure impossible. With an increased flexibility in the measurement procedure, the same result could be obtained by an OCT macula, an OCT optic nerve papilla recording and a 50 degrees fundus recording, even for an eye not in the state dilated by drops. Although only one further set could be defined by precisely this alternative measurement procedure, the number of measurement procedures for covering the combinations occurring in practice very quickly becomes unclear. The invention is directed to a solution to the aforementioned problems, which easily and cost-effectively improves the recording quality of the individual modalities of a combination instrument made of fundus camera and OCT system and also ensures the flexibility of such a combination instrument, without increasing the operational complexity thereof.

The object is achieved by a device and method consisting of a fundus camera with an OCT measurement module, in which, after the focusing objective, a mirror switches the light to be detected either to the OCT measurement module or to an image detector.

DETAILED DESCRIPTION

Figure 1:
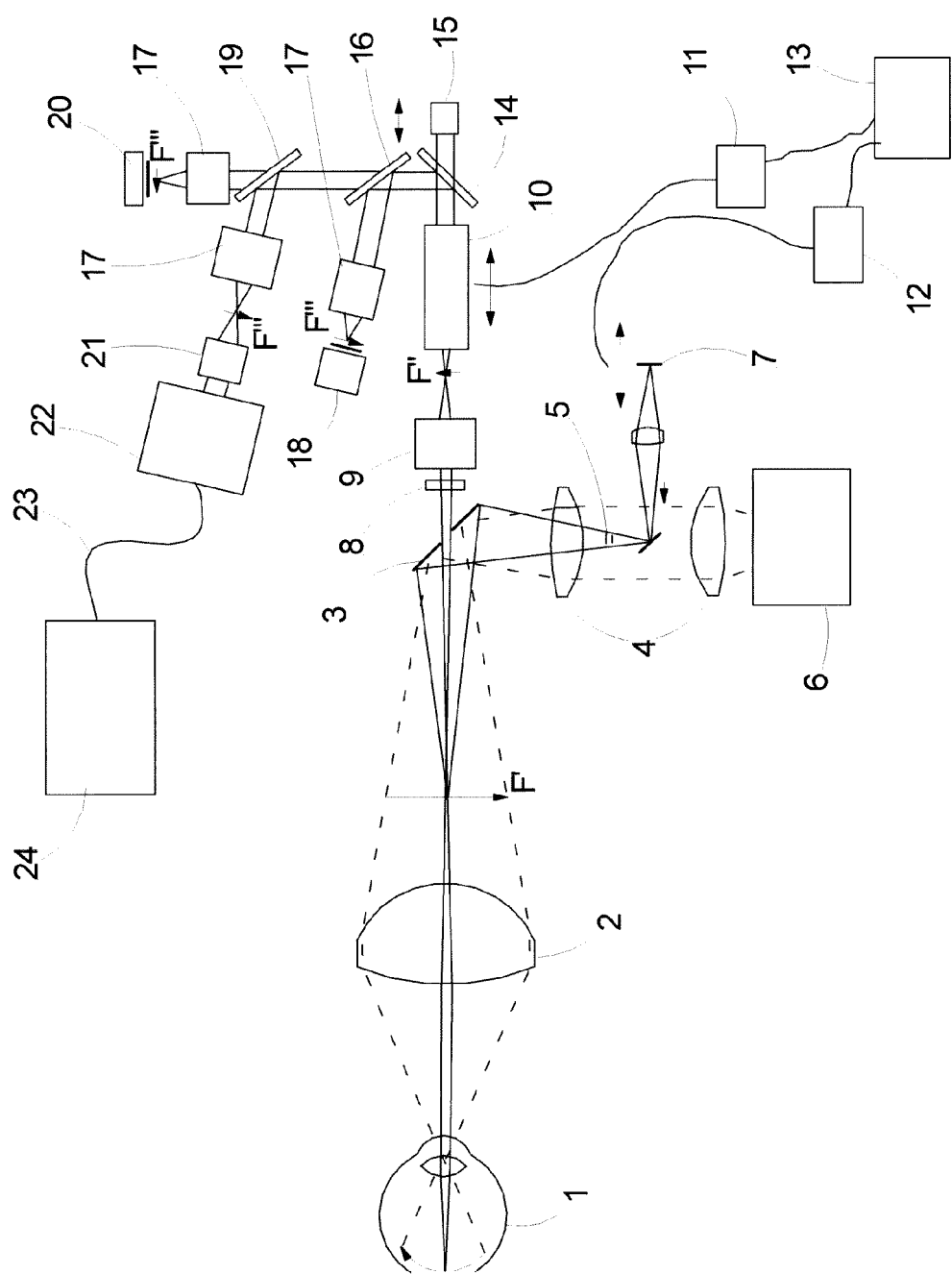
FIG. 1 is a schematic depiction of a device according to an example embodiment of the invention.

An example device according to the invention will be described using FIG. 1. FIG. 1 depicts a fundus camera with opthalmoscope lens 2, holed mirror 3, focusing objective 10, camera 18 and flash-light source 6 with antireflection points 5. During the fundus recording, the light flash is directed to the eye 1 fundus via the holed mirror 3. Here, the illumination optical unit 6 is designed such that an annular illumination aperture is created in the pupil of the eye 1 and this prevents the corneal apex from being illuminated and generating an interfering image reflection. The antireflection points 5 prevent light which is reflected at the opthalmoscope lens 2 and could interfere in the image from even entering the detection beam path. The light reflected by the retina is imaged by the opthalmoscope lens 2 in an intermediate image, which is then captured by the focusing objective 10 and transmitted on to an imaging objective 17 by the mirror 16 (in the position A thereof) inserted into the beam path. This then generates an image of the retina on a 2D sensor 18.

In order to support focusing, a test marker is present, which is imaged on the retina by two different, laterally separated optical paths in the IR light and therefore generates 2 half-marks in the region of the retina. The focusing objective 10 and the test marker are now adjusted together when focusing the overall instrument so that both half-marks are imaged in coincidence both on the retina and on the camera 18.

Furthermore, the device exhibits an OCT module 24 consisting of a light source, an interferometer and a detector, with the individual components not being shown individually in FIG. 1. Depending on whether this is a so-called time domain OCT method, spectral domain OCT method or swept source OCT method, this module is designed according to the already known prior art.

This OCT module 24 is coupled to the fundus camera by a fiber 23. The OCT illumination light is cast onto the retina through this fiber 23, the scanning mirror 22, the scanning objective 21, a field objective and in the case of a pushed-out mirror 16 (in the position B thereof). The scanning objective 21 together with the focusing objective 10 ensures that the image plane, and hence also the retina, is illuminated point-by-point in a focused scanning manner. The light reflected by the retina is coupled back—now in the reverse direction—into the fiber 23 through the illumination path, superposed with the reference signal in the OCT module 24 and detected, and an OCT signal of the retina is generated thus.

Hence, in accordance with FIG. 1, the mirror 16 switches between a fundus recording and an OCT measurement.

In the prior art—see U.S. Pat. No. 5,537,162 or else US 2007/222946—there is no switching by application of a mirror 16, but rather use is made of a dichroic mirror.

The use of a dichroic mirror is expedient to enable a simultaneous or overlapping measurement, or measurements following in quick succession, of a fundus recording and an OCT recording. However, in an instrument designed for several modalities with different wavelength requirements, this separation is not complete, and so a lower signal of the individual modalities has to be expected compared to a solution with a switchable mirror 16. This disadvantage also remains if the measurements of the various modalities are not simultaneous but sequential.

An additional issue occurring in the case of a simultaneous recording of various modalities furthermore is that the illumination intensity of the individual modalities, and hence also the signal, has to be selected to be lower than in the case of a sequential recording. In order to avoid damage to the eye 1, the overall intensity of all light simultaneously incident on the eye 1 must not exceed a certain threshold. In this case, the intensity load over the whole wavelength range potentially damaging to the eye 1 has to be taken into account, which, in the case of a combination instrument with simultaneous recording of different modalities, comprises both the visible range and also the near infrared range and hence also the OCT illumination. Hence this maximum illumination intensity must be distributed between the modalities in the case of a simultaneous OCT measurement and fundus recording. Therefore the illumination intensity is lower than in the case of a measurement with in each case only one intensity and it follows that the measurement signal is also lower.

In principle, this signal could be increased by a longer measurement time for the recording. However, this can only be realized to a restricted extent because otherwise the eye 1 movement and/or the pupil reflex would lead to a reduction in the image quality.

The use of a switchable mirror 16 now necessarily requires a sequential recording of the fundus and OCT recordings. This sequential procedure of the recordings now, in a further embodiment, enables the focus positions of the fundus recordings and the OCT measurements to be set independently of one another. If the individual fundus recordings of the color, angiography, autofluorescence and macula pigment density modalities are also carried out in sequence, the focus position for each one of the modalities can be individually set in an optimal manner.

By way of example, if the camera in the IR live mode is focused in relation to the eye 1 by application of the focusing aid and, to this end, the focusing aid is positioned with the linear encoder 1 11, see FIG. 1, it should be noted that the IR light, since it penetrates deeper into the tissue, is reflected at other points than e.g. on the surface of the retina. However, if one wishes to image this retina surface in focus in the OCT or in the color image, the linear encoder 2 12 can, while having the same setting of the focusing aid for OCT and the fundus recording, set the axial position of the focusing objective 10 in such a way that the retina is in focus in the OCT or in the fundus image. Here, the position of the focusing objective 10 when the retina is focused best in the color image will differ from the position of the focusing objective 10 when the retina is focused best in the OCT, already because of the chromatic aperture in the eye 1. A further example relates to autofluorescence recordings of lipofuscin, during which the RPE is put into focus, or to RNFL thickness measurements by means of OCT, during which the outer retina layers should be in focus.

Also, different focus positions can be set, even for one modality, in order to be able to record different structures to be examined with optimum lateral resolution. An example includes OCT measurements of the retina compared to OCT measurements of the choroid.

It is now particularly advantageous if the detection beam path has a telecentric design for all modalities. As a result, refocusing from one modality to the other is not accompanied by a change in the image size. Therefore, OCT data and fundus images can be compared to one another without further lateral scaling. This is important to the extent that in the case of sequential OCT, measurement and fundus images have to be compared to one another and also fundus images from different focal positions have to be compared to one another and be laterally registered to one another. By contrast, in the case of simultaneous recordings, the various recordings or measurements are already measured registered to one another. As a result of a different lateral scaling of the data to be registered to one another, in addition to the lateral displacement, it becomes more difficult to find correlations between both sets of data and the lateral registration to one another deteriorates.

Furthermore, as shown in the image on the basis of the beam splitter 14 for coupling in the fixation light, it is recommended that the OCT signal, where possible, does not pass through a dichroic beam splitter but at best is reflected thereon. As a result of this, it is possible to minimize polarization effects, which are generated when the OCT signal passes through dichroic beam splitters and have a negative influence on the OCT signal. The design described in FIG. 1 also renders it possible to carry out a method (A) for improved focusing in order to improve the recording quality of the individual modalities. Independently of this design described in FIG. 1, this method for improved focusing of a multimodal retinal image recording system, according to the invention, consists of the following steps:

1. focusing the focusing marker and the focusing objective 10 on the basis of IR live recordings of the focusing marker; storing the axial position of the focusing objective 10 as reference position,
2. adjusting the axial position of the focusing objective 10 by a fixedly predetermined offset in relation to the reference position for the purposes of focusing for the OCT measurement, optionally taking into account the fixedly predetermined depth position of the examination object,
3. switching a mirror 16 from IR live mode to OCT measurement,
4. performing an OCT measurement, for example of a slice image,
5. optionally renewed adjusting of the axial position of the focusing objective 10 by a further fixedly predetermined offset relative to the reference position for the purposes of focusing the OCT measurement to a fixedly predetermined depth position of the new examination object and renewed OCT measurement,
6. adjusting the axial position of the focusing objective 10 by a further predetermined value relative to the reference position for the purposes of focusing for a fundus recording,
7. switching the mirror 16 from OCT measurement to fundus recording,
8. fundus recording,
9. optionally renewed adjusting of the axial position of the focusing objective 10 by a further fixedly predetermined offset relative to the reference position for the purposes of focusing the fundus camera for a new fundus camera modality, e.g. angiography or autofluorescence, and renewed fundus recording.

To the extent that the patient's eye 1 is in a state dilated by drops, the sequence of steps in relation to the individual modalities can also be modified. The predetermined values relate to an offset in the axial direction, which depends on the measurement modality and optionally on the examination object. In a further embodiment of the method, the specific depth position of the structure to be examined in the eye 1 can be determined by the OCT. This information can then be employed to set the offset of the focusing objective 10 in relation to the reference position in such a way that the structure to be examined lies in the focus and the highest focus can be set for this structure in the case of a fundus recording. Here, the OCT measurement for determining the depth position can already be known from a previous OCT measurement or the OCT measurement can occur for the first time within the scope of the focusing process. Thus, for example, the depth position of the RPE, which represents the main reflection layer in the IR and to which the focus is set in the IR, can be determined in relation to the retinal surface in the OCT and it is then possible to set the axial position of the focusing objective 10 for the fundus recording, in a corresponding person-specific manner fitted to the structure to be examined. Independently of the method steps above, or else as an alternative embodiment of partial step 1 of the method above, the positioning of the instrument and/or the focusing of 2D fundus recordings on the plane of the reference value can be carried out, not only on the basis of the focusing marker, but additionally on the basis of OCT measurements themselves, or only on the basis thereof in the case of sufficient scanning depth of said OCT. To this end, the distance of the cornea and/or of the retina from the instrument is determined on the basis of a pre-setting OCT scanning grid or else only on the basis of the A-scan. In the process, it may optionally be necessary to switch between an anterior chamber mode and a posterior chamber mode in the OCT in order to achieve the necessary scanning depth. If it is not possible to determine the distance or if the established distance lies outside of a predetermined range for the cornea or the retina, the user is provided with a notification in relation to this axial deviation and additionally provided with a notification in respect of necessary changes in the positioning of the camera or the focusing. In the process, the axial positioning of the camera in relation to the cornea is determined on the basis of the corneal position in the OCT signal. By contrast, the focusing of the focusing objective 10 is determined by the retina position in the OCT signal. Instead of a notification in respect of the direction of the necessary changes in the alignment of the instruments or the focus, it is also possible, in the case of automated instruments, for the overall instrument to be positioned automatically on the basis of the corneal position in the OCT signal (auto-alignment) or for the focusing objective 10 to be set automatically (autofocus). Hence this embodiment of the method for improved focusing or positioning of a multimodal retina image recording system contains the following steps:

a) optionally switching to the OCT anterior chamber measurement mode,
b) OCT measurement and determining the position of the cornea,
c) matching the determined corneal position to the intended position range,
d) providing the corneal position lies outside of the intended position range: notification to the user and/or automatic axial displacement of the whole instrument,
e) repeating steps a-d until the corneal OCT position lies in the intended position range,
f) optionally switching to the OCT posterior chamber mode,
g) OCT measurement and determining the position of the retina,
h) matching the determined retina position to the intended position range,
i) providing the retina position lies outside of the intended position range: notification to user and/or automatic axial displacement of the focusing objective 10,
j) repeating steps j-l until the retina OCT position in the intended position range,
k) adjustment and focusing complete. In a variant of method A above, the steps a)-e) or f)-j) or else all steps a)-j) can be used to complement the conventional positioning and focusing methods in step 1 of method A. All the methods for optimizing the focus position described above can also be carried out if, in place of the switchable mirror 16, use is made of a fixed dichroic mirror but the measurements in relation to the individual modalities—like in the embodiment with a switchable mirror 16—continue to occur in sequence.

In order to enable a secure and, in terms of application, flexible operation by the user despite the complexity of the multimodal instrument sketched out above, a simple, clear, intuitive operating concept is required. Here, the operation should enable both the control of the instrument for recording multimodal data and also the evaluation thereof.

Figure 2:
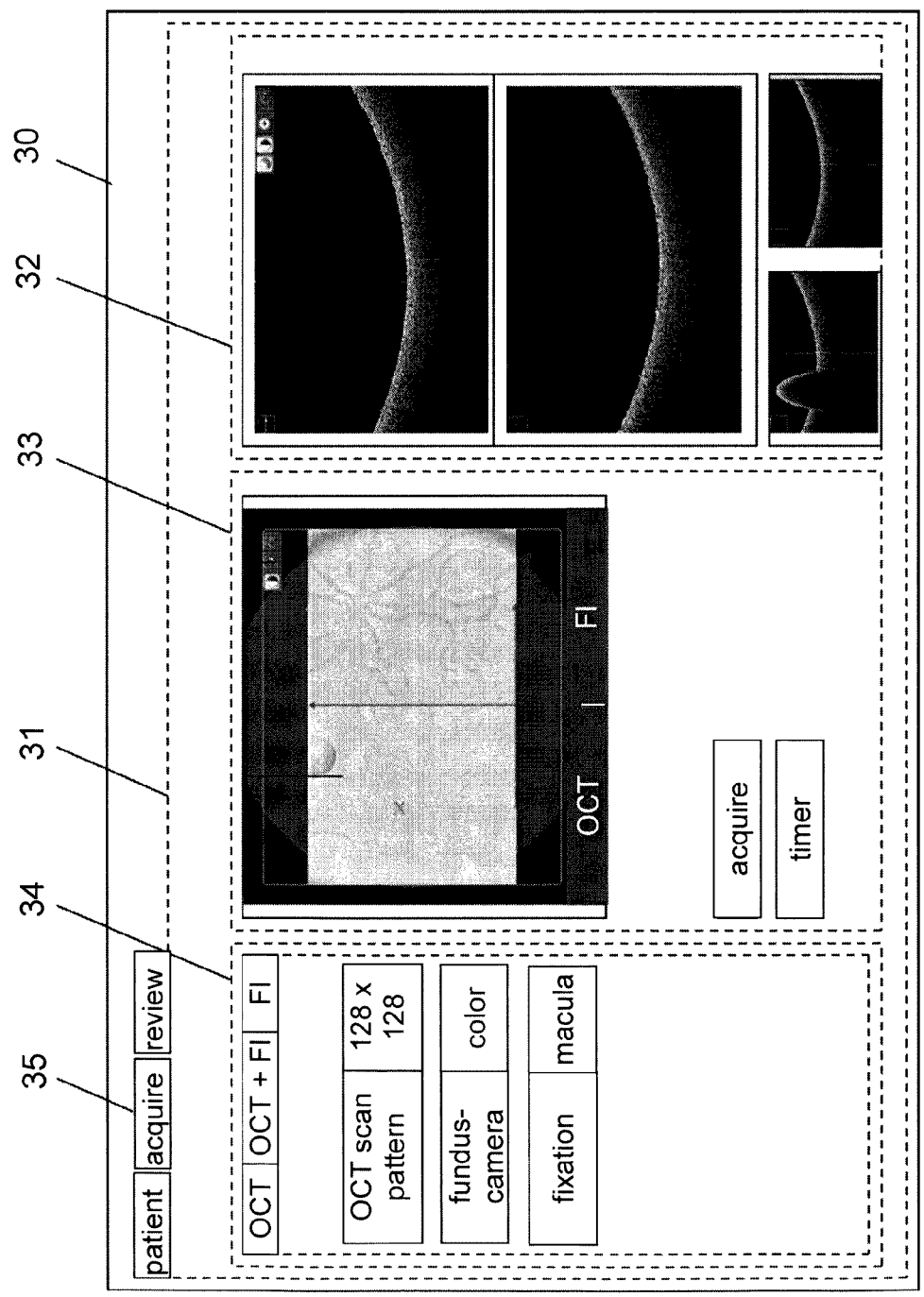
FIG. 2 depicts a screen for an operating concept according to an example embodiment of the invention.
Figure 3:
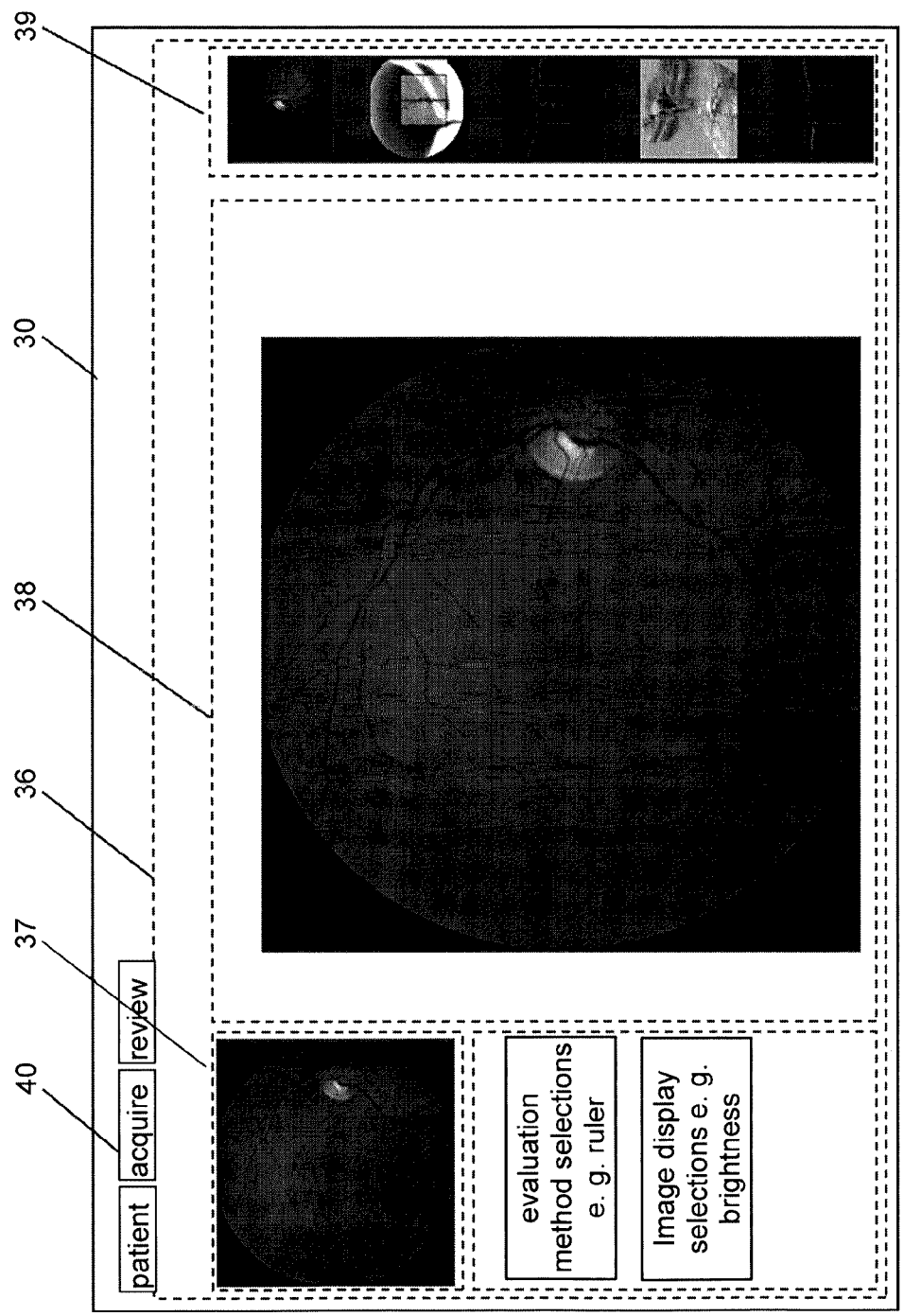
FIG. 3 depicts a screen for an operating concept according to an example embodiment of the invention.

This operating concept according to the invention of the multimodal measuring instrument is characterized by (see FIGS. 2 and 3):

a screen-filling recording region 31 and a screen-filling image observation region/analysis region 36, wherein it is possible to switch between the two regions by a single user action, for example a mouse click or pressing precisely one pushbutton with the finger, a recording region 31 consisting of an a measuring instrument control region 34 and a first and a second image display region 33, a measuring instrument control region 34, in which a fundus recording mode, an OCT recording mode and a combination recording mode is characterized by a tab, in which all measurement parameters to be specified by the user for setting this mode prior to the recording, and only these, are listed, wherein these parameters are the same as the ones that the user is used to from the separate measuring instruments for the corresponding measurement modality, wherein each mode/tab has its own measurement parameter set, even if the same modality occurs again in another recording mode. If the recording button associated with the first image display region 32 is activated when the combination recording mode is selected (by selecting the corresponding tab), then the OCT recording is made first and this is followed immediately, without further user interaction, by the fundus recording, a first image display region 32 for displaying 2D images which are necessary for setting the respective selected measurement mode. These are, for example, the IR live images for positioning and focusing the instrument and images for setting or displaying the OCT scan line in the 2D image (IR live images from the camera or else the IR live LoReFo image or else a still frame), wherein the control elements to be operated by the user during the recording or the adjustment, such as the recording triggering or a clock required for angiography, are assigned to this first image display region 32. This image display region 32 also serves for displaying the recorded (still frame) 2D fundus recordings, a second image display region 33, situated next to the first image display region 32, for displaying OCT slice images from both the still frames and from live images, an image observation/analysis region 36 consisting of an overview region for displaying an overview image 37 of the fundus, an image region 38 for looking at, analyzing an image and/or comparing several images or segments of images—whether these are fundus or OCT images, and a library display region 39, in which all images of a patient are accessible and are selected for displaying in the overview region and image region 38. The advantage of this recording region 31 structured and designed in this way in relation to the prior art lies in that, firstly, there is clear separation between the modalities in relation to the control such that, for example, a user not trained in OCT operation only operates the operating elements for the fundus recording and is only presented with information in relation to the fundus recording and is therefore not unnecessarily confused. Secondly, the simple switching between the tabs enables an experienced user to switch very quickly between the individual modalities and, in the process, also immediately see the measurement parameters thereof being displayed. Furthermore, the combination recording mode also allows the experienced user to record several modalities from a single trigger, which saves switching between the modalities and renewed alignment and focusing of the instrument.

Furthermore, the operating concept presented above is characterized by a few peculiarities, which relate to the transition from the recording region 31 into the image observation region/analysis region 36—and vice versa—and which simplify daily operation:

1. Thus, in the transition from the image observation region/analysis region 36 to the recording region 31 of the OCT mode or of the combination recording mode, the fundus image, which is last/currently selected in the image observation region/analysis region, is transferred into the observation region of the recording region 31.

2. Conversely, in the transition from the recording region 31 into the image observation region/analysis region 36, the current image of the observation region of the recording region 31 is transferred into the overview region and the image region 38 of the observation region/analysis region 36. The advantage of these aspects of the operating concept lies in the simple initiation of the transfer of images from the recording mode into the image display/analysis mode, and vice versa, in order quickly to be able to continue work in the respective future mode. The image required for continuing work in the future mode need not be realized by loading/importing or clicking the desired image but rather occurs automatically. Thus, an image from a preceding measurement, which was analyzed in the image region 38 of the observation region/analysis region 36 and in which a peculiarity, which should be measured again in more detail, was determined, is will be immediately presented as preset image in the first image observation region of the recording region 31 in order, for example, to position the OCT scanning grid over the peculiarity.

This scanning pattern is then used during the OCT recording after registering the analysis image to the live image. If the patient needs to be reaffixed in the process for the OCT, this is carried out automatically.

In the following text, 2 aspects shall still be discussed in detail, which, in the implementation of the device described in FIG. 1, have to be achieved in a cost-effective manner in order to secure the higher measurement value quality achieved by the measures above.

In order to achieve very high sensitivities in the OCT, the reference and the radiation reflected by the object must be aligned precisely to one another, even in respect of polarization. This often occurs by virtue of a so-called paddle being installed in one of the two beam paths which, depending on the position of this paddle, changes the polarization. By an appropriate setting of the paddle the polarization of the reference beam and the object beam is aligned in parallel in order to obtain a signal contrast which is as high as possible. In the system shown in sketch 1, it was found that, as a result of the long optical paths between short-coherent light source and the interferometric superposition of reference and object beam, the polarization of the object signal in the uncompensated for state deviates very strongly from the optimum polarization direction and, as a result of the position which is not always the same of the external supply fiber, for example as a result of inadvertent contact or when displacing the instrument, also has to be varied over a relatively large range. In order to implement the extended polarization adjustment range in a cost-efficient manner, two or more positioning grooves are firstly attached at the fiber end which leads to the measuring instrument. These grooves fit into one or more counterpoints of the fiber connector on the instrument. Naturally, it is also possible to attach the grooves to the instrument and the counterpoints to the fiber end or to use the OCT module 24 in place of the instrument—as a result of this, it is possible, by the appropriate selection of the fiber grooves which are placed onto the counterpoints, to undertake different settings which vary in the rotational direction thereof. As a result, it is possible to preset the order of magnitude of the necessary polarization rotation. The paddle, which continues to be present, is then, in terms of its variable circumference, only designed in such a way that it covers the variations occurring during normal operation. In particular, it was found that 2 paddles are advantageous. For a high measurement value quality, a correct registration of the 2D fundus images in relation to the OCT data is also necessary. As already mentioned above, the OCT measurement data and the 2D fundus data have to be registered to one another in the case of a sequential measurement since they are not recorded registered to one another. This is advantageously brought about by the calculation of a so-called en-face image from the OCT B-scan measurement values. This is a 2D image which is calculated by a reduction of the data along the OCT axis. Here, the reduction along the z-axis can take place e.g. as projection, maximum intensity or intensity of a specific retinal structure. Hence the en-face image is directly registered to the 3D OCT data set.

The 2D fundus image is now registered to the 2D en-face image. Here, there is both a lateral and a distortion correction on the basis of the structures found in both images.

In the combined output of both images, e.g. in a side-by-side display, the 2D fundus image is then shown in the version registered to the en-face image. Compared to the variant which is to transform the OCT data of the on of the fundus image, this variant is advantageous in that the distortions in the fundus image, as a result of the high resolution of the fundus image, do not lead to a significant perceivable change in the local resolution in the transformed fundus image. By contrast, if the transform is carried out in reverse, if a B-scan is displayed through a transformed 3D OCT data record, there will have to be significant and irregular interpolation for the individual pixels since the lateral resolution of the OCT is by no means as high as that of a 2D fundus image.

Structures depicted in the attached drawings are labeled as follows:
1 Eye
2 Ophthalmoscope lens
3 Holed mirror
4 ARP objective
5 Antireflection points (ARP)
6 Illumination unit
7 Focusing mask
8 Band-elimination filter
9 Main objective
10 Focusing objective
11 Linear encoder 1
12 Linear encoder 2
13 Control instrument
14 Beam splitter
15 Light sensor
16 Mirror
17 Imaging objective
18 Camera/2D sensor
19 Beam splitter
20 Fixation target
21 Scanning objective
22 Scanning mirror
23 Optical fiber
24 OCT module
30 Screen
31 Recording region
32 First image display region
33 Second image display region
34 Measuring instrument control region
35 Switch to the recording region
36 Observation region and analysis region
37 Overview image
38 Image region
39 Library region
40 Switch to the observation region and analysis region

The invention claimed is:

1. A device for multimodal image recording and measuring of the retina, comprising:
   a fundus camera having an OCT measurement module and a control unit;
wherein a mirror is located following a focusing objective and the mirror, controlled by the control unit, is shiftable between a first position and a second position and switches light to be detected either to the OCT measurement module or to an image detector of the fundus camera; and
   a first electronic path actuator that axially positions a focusing marker and a second electronic path actuator that axially positions the focusing objective under control of the control unit and wherein the control unit, when the control unit shifts the mirror, also changes a position of the second path actuator, but not the first path actuator.

2. A device for multimodal image recording and measuring of the retina, comprising:
   a fundus camera having an OCT measurement module and a control unit;
wherein a mirror is located following a focusing objective and the mirror, controlled by the control unit, is shiftable between a first position and a second position and switches light to be detected either to the OCT measurement module or to an image detector of the fundus camera;
   wherein the fundus camera has a telecentric detection beam path.

3. The device as claimed in claim 1, wherein the fundus camera has a telecentric detection beam path.

4. A method of focusing individual modalities of a multimodal retinal image recording system, comprising:
   focusing a focusing marker and a focusing objective based on IR live recordings of the focusing marker;
   storing an axial position of the focusing objective as reference position;
   adjusting the axial position of the focusing objective by a fixedly predetermined offset in relation to the reference position to focus for an OCT recording mode;
   switching a mirror from IR live mode to OCT recording mode;
   performing an OCT recording;
   adjusting the axial position of the focusing objective by a further fixedly predetermined offset relative to the reference position to focus for a 2D imaging mode;

switching the mirror from OCT mode to 2D imaging mode;
making a 2D imaging recording.

5. The method as claimed in claim 4, wherein the offset of the position of the focusing objective is set on the basis of the depth position of a structure in the OCT image.

6. The method as claimed in claim 4, wherein adjusting the axial position of the focusing objective further comprises taking into account the fixedly predetermined depth position of the structure to be examined.

7. The method as claimed in claim 4, wherein performing an OCT recording further comprises recording of a slice image.

8. The method as claimed in claim 4, further comprising renewed adjusting of the axial position of the focusing objective by a further fixedly predetermined offset relative to the reference position to focus the OCT mode to the fixedly predetermined depth position of the new structure to be examined and renewed OCT recording.

9. The method as claimed in claim 4, wherein the 2D imaging mode comprises color imaging using a shift table.

10. The method as claimed in claim 4, further comprising adjusting of the axial position of the focusing objective by a further fixedly predetermined offset relative to the reference position for the purposes of focusing the fundus camera for a new fundus camera modality.

11. The method as claimed in claim 10, wherein the new fundus cameral modality is selected from the group consisting of: angiography, autofluorescence, and renewed fundus recording.

12. A method of positioning and focusing a multimodal retina image recording system, comprising:
 a) switching to an OCT anterior chamber measurement mode if not already in the OCT anterior chamber measurement mode;
 b) making an OCT measurement and determining a position of a cornea;
 c) matching a determined corneal position to an intended position range;
 d) if the corneal position lies outside of the intended position range, notifying a user and/or automatic axially displacing a whole instrument;
 e) repeating steps a-d until the corneal OCT position lies within the intended position range;
 f) switching to the OCT posterior chamber mode if not already in the OCT posterior chamber mode,
 g) making another OCT measurement and determining a position of a retina,
 h) matching a determined retina position to the intended position range,
 i) if the retina position lies outside of the intended position range, notifying the user and/or automatic axially displacing a focusing objective;
 j) repeating steps f-i until the retina OCT position lies in the intended position range; and
 k) adopting the obtained axial position of the focusing objective as reference position.

* * * * *

UNITED STATES PATENT AND TRADEMARK OFFICE
CERTIFICATE OF CORRECTION

PATENT NO. : 9,532,710 B2
APPLICATION NO. : 14/441108
DATED : January 3, 2017
INVENTOR(S) : Detlef Biernat et al.

Page 1 of 1

It is certified that error appears in the above-identified patent and that said Letters Patent is hereby corrected as shown below:

In the Claims

Column 6, Line 63, delete "j-l" and insert --f-i--

Column 7, Line 22, delete "an"

Column 9, Line 42, delete "on of the"

Signed and Sealed this
Twenty-first Day of November, 2017

Joseph Matal
*Performing the Functions and Duties of the
Under Secretary of Commerce for Intellectual Property and
Director of the United States Patent and Trademark Office*